United States Patent
Walters

(10) Patent No.: US 6,880,957 B2
(45) Date of Patent: Apr. 19, 2005

(54) LIGHTING APPARATUS WITH ELECTRONIC SHADOW COMPENSATION

(76) Inventor: Mark Wayne Walters, 652 Epps Rd., P.O. Box 516, Palmer, Ellis County, TX (US) 75152

(*) Notice: Subject to any disclaimer, the term of this patent is extended or adjusted under 35 U.S.C. 154(b) by 167 days.

(21) Appl. No.: 10/108,811

(22) Filed: Mar. 28, 2002

(65) Prior Publication Data

US 2003/0185009 A1 Oct. 2, 2003

(51) Int. Cl.$^7$ ............................................. F21V 25/12
(52) U.S. Cl. ..................... 362/276; 362/33; 362/231; 362/227; 362/285; 315/152; 250/205
(58) Field of Search ..................... 362/276, 33, 231, 362/285, 227, 105, 183, 583, 255, 286, 304; 315/152; 250/205

(56) References Cited

U.S. PATENT DOCUMENTS

| | | | |
|---|---|---|---|
| 3,967,107 A | | 6/1976 | Junginger et al. |
| 4,009,387 A | | 2/1977 | Nuver |
| 4,622,625 A | * | 11/1986 | Becker et al. ............... 362/304 |
| 4,701,669 A | | 10/1987 | Head et al. |
| 4,884,008 A | * | 11/1989 | Bossler et al. ............... 315/152 |
| 4,937,714 A | * | 6/1990 | Witt ............................ 362/255 |
| 5,038,261 A | * | 8/1991 | Kloos ........................ 362/286 |
| 5,461,551 A | * | 10/1995 | Clayton ...................... 362/183 |
| 6,196,703 B1 | * | 3/2001 | Eusterbrock et al. ........ 362/276 |
| 6,322,226 B1 | * | 11/2001 | Dickson ....................... 362/33 |
| 6,513,962 B1 | * | 2/2003 | Mayshack et al. ........... 362/583 |
| 2001/0014019 A1 | * | 8/2001 | Begemann ................... 362/231 |
| 2002/0085372 A1 | * | 7/2002 | Lehrer ......................... 362/105 |

FOREIGN PATENT DOCUMENTS

| | | |
|---|---|---|
| DE | 299 09 064 U1 | 8/1999 |
| DE | 198 12 555 A1 | 9/1999 |
| FR | 2 752 912 | 3/1998 |

* cited by examiner

Primary Examiner—Stephen Husar
Assistant Examiner—James Cranson
(74) Attorney, Agent, or Firm—Andrew J. Dillon; Dillon & Yudell LLP

(57) ABSTRACT

An electronic lighting apparatus with at least one multiple position adjustable lighting pod. Each lighting pod includes at least one variable intensity light source and a proximity sensor for detecting objects interposed between the lighting pod and a work field. Each variable intensity light source is powered by a controllable pulse width modulated power supply or other suitable power supply which can be utilized to vary the intensity of the light source. In response to detection of an object interposed between a particular lighting pod and the work surface, the power to that lighting pod is increased, increasing the illumination of the work field. Alternatively, power to that lighting pod may be decreased and power to alternate lighting pods is increased, thereby minimizing shadows within the work field.

16 Claims, 4 Drawing Sheets

LIGHTING APPARATUS WITH ELECTRONIC SHADOW COMPENSATION

BACKGROUND OF THE INVENTION

1. Technical Field

The present invention relates in general to an improved lighting apparatus and in particular to an improved lighting apparatus which minimizes shadows within an illuminated work field. Still more particularly the present invention relates to an improved lighting apparatus with electronic shadow compensation which minimizes shadows within an illuminated work field by automatically varying the intensity of separate lighting pods within the lighting apparatus.

2. Description of the Related Art

Lighting systems which illuminate a work field with a minimum amount of shadows are highly desired in many environments. In particular, the utilization of such lighting systems for the surgical work fields, examination room lighting or other medical applications is well known in the prior art.

Conventionally, so-called "shadow-free" lamps typically include a parabolic reflector or prismatic lenses which are coupled with a linear light source. The position of the linear light source and the parabolic reflector or prismatic lenses are designed so that the system produces a specified irradiation pattern in order to illuminate a particular portion of the work field in an effort to produce a shadow-free work field even if selected rays of light are partially intercepted by the interposition of an object between the light and the work field.

As medical technology has become more complex, lighting systems have advanced as well. Typically, multiple light fixtures with multiple reflectors are now commonly utilized to project cylindrical light rays in an effort to minimize shadows within the work field. Systems exist which automatically focus the illumination from such a lighting system onto a desired area of the work field, either automatically or in response to a manual reposition of the lighting apparatus.

Consequently, it would be desirable to produce a lighting fixture which minimizes the amount of shadow within the work field caused by the interposition of an object between the lighting apparatus and the work field without requiring the complexity of physical repositioning apparatus or the necessity of continual manual relocation of the lighting fixture during a medical procedure.

SUMMARY OF THE INVENTION

It is, therefore, one object of the present invention to provide an improved lighting apparatus.

It is another object to the present invention to provide an improved lighting apparatus which minimizes shadows within an illuminated work field.

It is yet another object of the present invention to provide an improved lighting apparatus with electronic shadow compensation which minimizes shadows within a work field by varying the intensity of separate lighting pods within the lighting apparatus.

The foregoing objects are achieved as is now described. An electronic lighting apparatus is provided with at least one multiple position adjustable lighting pod. Each lighting pod includes at least one variable intensity light source and at least one proximity sensor for detecting objects interposed between the lighting pod and a work field. Each variable intensity light source is powered by a controllable pulse width modulated power supply or other suitable power supply which can be utilized to vary the intensity of the light source. In response to detection of an object interposed between a particular lighting pod and the work surface, the power to that lighting pod is increased, increasing the illumination of the work field. Alternatively, power to that lighting pod may be decreased and power to alternate lighting pods is increased, thereby minimizing shadows within the work field without requiring the lighting apparatus to be physically relocated.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
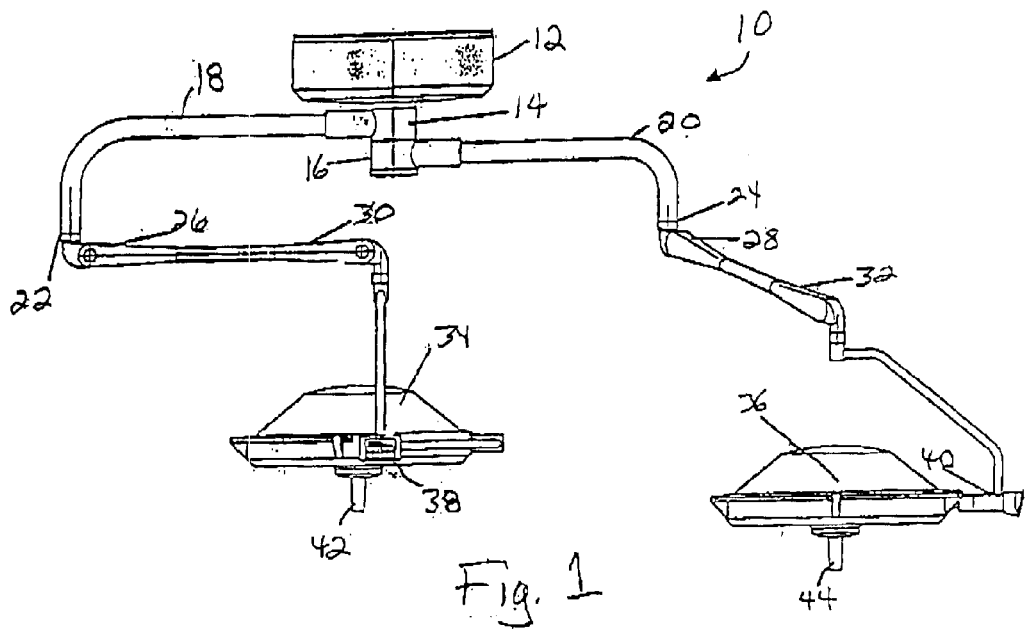
FIG. 1 is a pictorial representation of the improved lighting apparatus of the present invention.

With reference now to figures and in particular with reference to FIG. 1, there is depicted a pictorial representation of an improved lighting apparatus 10 constructed in accordance with one embodiment of the present invention. As illustrated, lighting apparatus 10 is mounted utilizing a ceiling mount 12. Of course, lighting apparatus 10 may be mounted to a wall or a mobile stand or by any other suitable means providing sufficiently rigid support. Mounted to the lower portion of ceiling mount 12 are swivel bearings 14 and 16 which are connected to mounting arms 18 and 20. As illustrated, mounting arms 18 and 20 may thus swivel on swivel bearing 14 and 16 respectively, allowing lighting apparatus 10 to be repositioned manually.

At the lower end of arms 18 and 20 are mounted swivels 22 and 24 which are connected to elbows 26 and 28. In accordance with a mounting technique well known in the prior art, elbows 26 and 28 are coupled via a short shaft to elbows 30 and 32. Lighting heads 34 and 36 are then mounted at the end of each articulated arm formed by the component parts described above by means of a swivel mount 38 and 40. Handles 42 and 44 provide a thermally insulated extension by which lighting heads 34 and 36 may be manually repositioned by a user of lighting apparatus 10.

Figure 2:
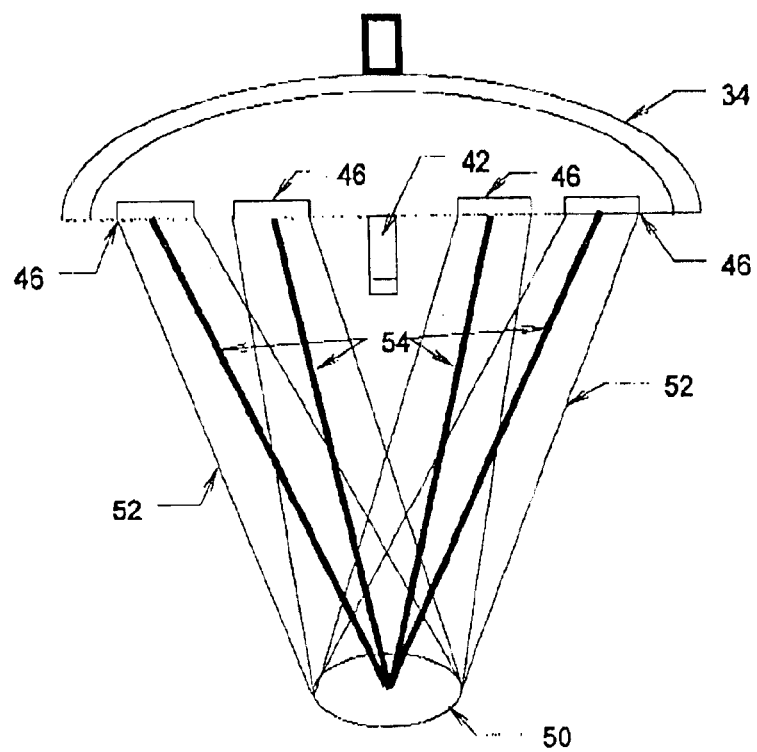
FIG. 2 is a schematic side view of a light head and multiple lighting pods within the lighting apparatus of FIG. 1.

Referring now to FIG. 2 there is depicted a schematic side view of a light head and multiple lighting pods within lighting apparatus 10 of FIG. 1. This view illustrates an important feature of the present invention. As depicted, multiple lighting pods 46 are mounted within each light head 34. Each lighting pod 46 is preferably mounted and focused so as to illuminate work field 50 from multiple angles with a light beam 52. That is, each lighting pod 46 is mounted along a radius extending from work field 50.

As illustrated, one important feature of the present invention involves the utilization of a proximity detector within each lighting pod 46. Each proximity detector (not shown) transmits a proximity sensor beam 54 which is focused within work field 50. Thus, if an object is interposed between a particular lighting pod 46 and work field 50, the proximity detector within each lighting pod will detect the presence of that object and modify the intensity of the output by each lighting pod in a manner which will be described in greater detail herein.

Figure 3:
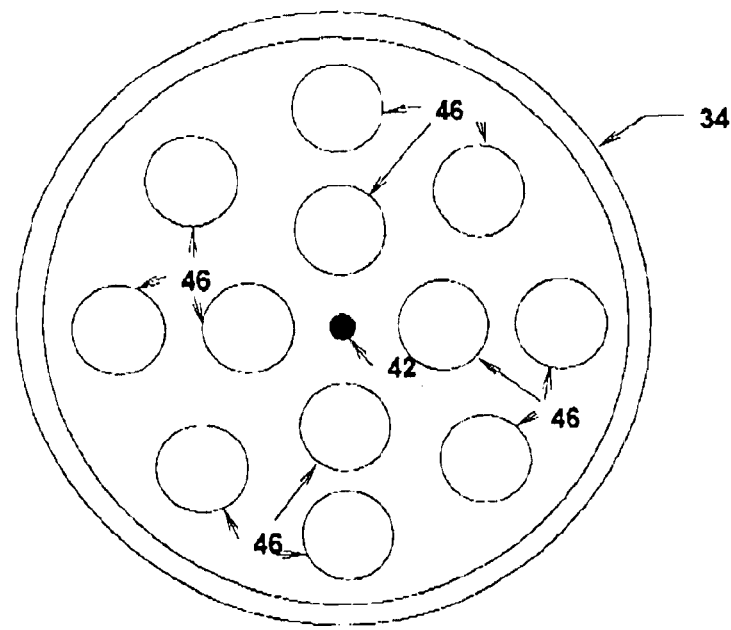
FIG. 3 is a schematic view of the bottom of the light head of FIG. 2 in accordance with the present invention.

With reference now to FIG. 3, there is depicted a schematic view of the bottom of light head 34 of FIG. 2. As illustrated, multiple lighting pods 46 are disposed within light head 34 in approximate equidistant positions surrounding handle 42. The number and shape of each lighting pod utilized is subject to design considerations and the number and configuration of lighting pods within light head 34 is for illustration purposes only.

Figure 4:
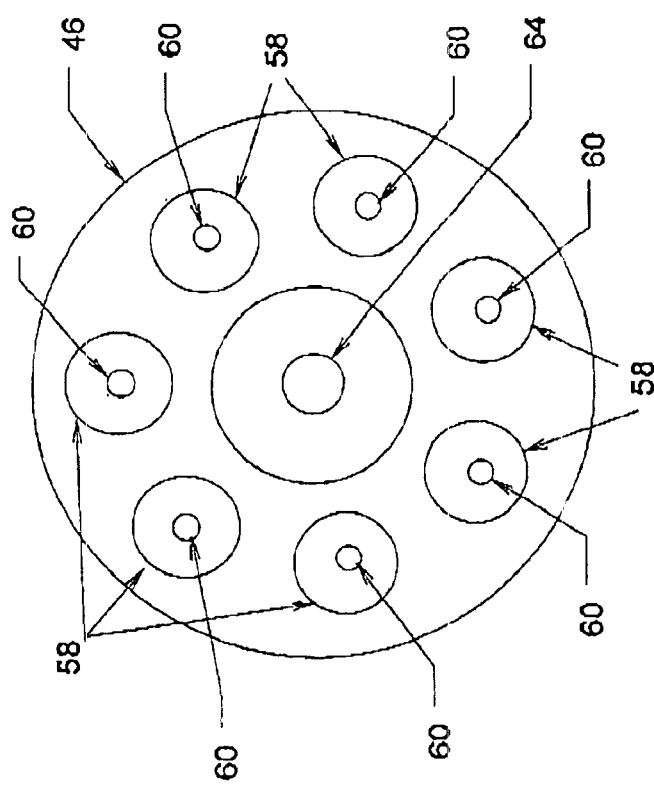
FIG. 4 is a schematic view of one embodiment of a lighting pod in accordance with the present invention.

Referring now to FIG. 4, there is depicted a schematic view of one embodiment of a lighting pod 46 in accordance with the present invention. As depicted, lighting pod 46 includes multiple reflector mounts 58, each of which contains one or more light emitting diodes 60. In this depicted embodiment of the present invention light emitting diodes 60 are preferably white light emitting diodes and each light emitting diode 60 may comprise one or more such light emitting diodes. Mounted in the center of lighting pod 46 is proximity detector 64. In one embodiment of the present invention, proximity detector 64 comprises an infrared proximity detector. In an alternate embodiment of the present invention proximity detector 64 comprises an ultrasonic proximity detector. Those skilled in the art will appreciate that any suitable technology whereby the presence of an object interposed between a lighting pod 46 and work field 50 may find application in the present invention.

Figure 5:
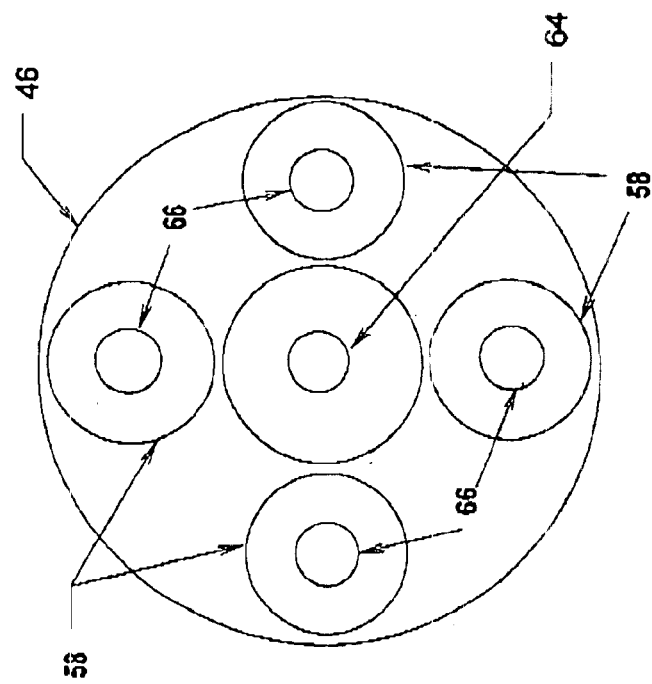
FIG. 5 is a schematic view of a second embodiment of a lighting pod in accordance with the present invention.

With reference now to FIG. 5, there is depicted a schematic view of a second embodiment of a lighting pod 46 in accordance with the present invention. In this depicted embodiment once again multiple reflector mounts 58 are provided, within each of each is mounted a halogen light source 66. Similarly, a proximity detector 64 is mounted in the center of lighting pod 46, and as noted above, proximity detector 64 may comprise any suitable means for detecting the placement of an object between lighting pod 46 and work field 50.

Figure 6:
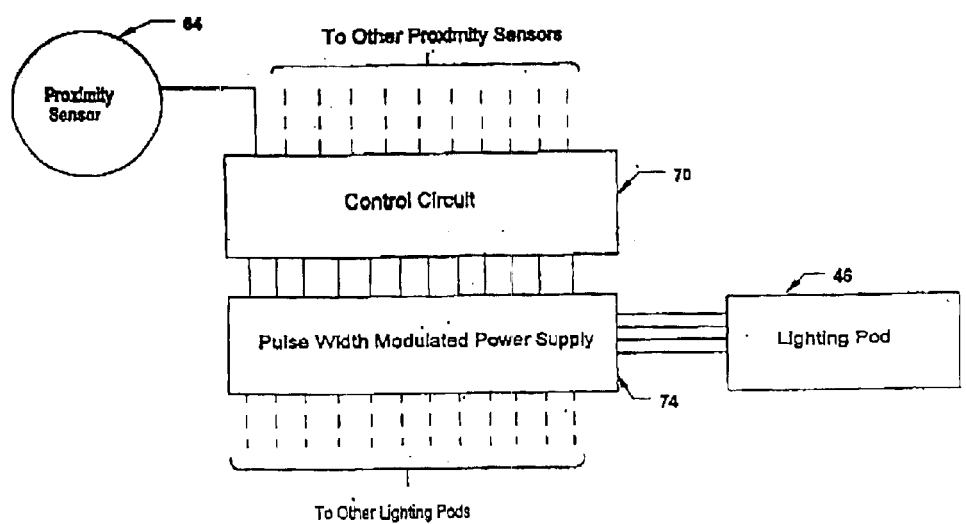
FIG. 6 is a schematic of a power control circuit utilized to vary the intensity of the output of each lighting pod in accordance with the present invention.

Referring now to FIG. 6, there is depicted a schematic of a power control circuit which may be utilized to vary the intensity of the output of each lighting pod within lighting apparatus 10 of the present invention. As depicted, the output of each proximity sensor 64 is coupled to a control circuit 60. Control circuit 60 constitutes a simple comparator circuit for determining whether or not the output of proximity sensor 64 indicates the presence of an object interposed between a lighting pod 46 and work field 50.

Next, control circuit 70 generates an output for each lighting pod which is coupled to pulse width modulated power supply 74. In the depicted embodiment of the present invention pulse width modulated power supply 74 generates variable pulse width voltage pulses which are coupled to the individual lighting elements within each lighting pod 46. Of course, alternate power supply arrangements are possible, dependent upon the type and number of lighting pods utilized. Although one lighting pod 46 is depicted for purposes of illustration, those having ordinary skill in the art will appreciate that multiple lighting pods may be utilized and multiple output lines are coupled to each lighting pod within lighting apparatus 10.

Thus, as will be explained in greater detail herein with respect to FIG. 7a-7c, the amount of voltage applied to the light source within each lighting pod 46 may be systematically varied in accordance with the presence or absence of an object interposed between a lighting pod and work field 50, minimizing the amount of shadow present within work field 50.

Figure 7A:
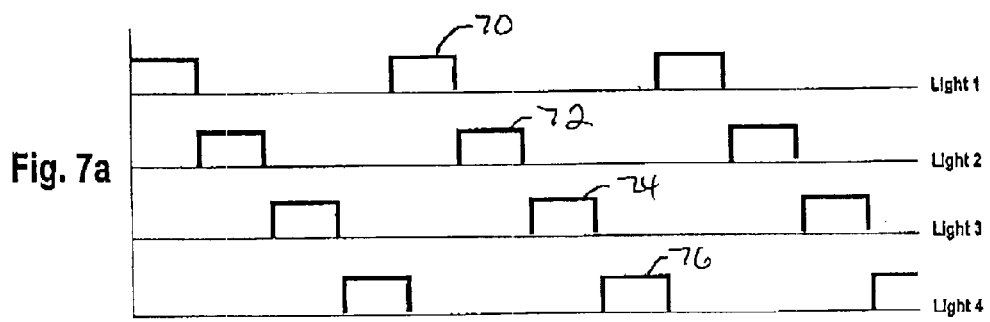
FIGS. 7a-7c are timing diagrams illustrating the timing of application of electrical power to multiple light sources within each lighting pod in accordance with the present invention.
Figure 7B:
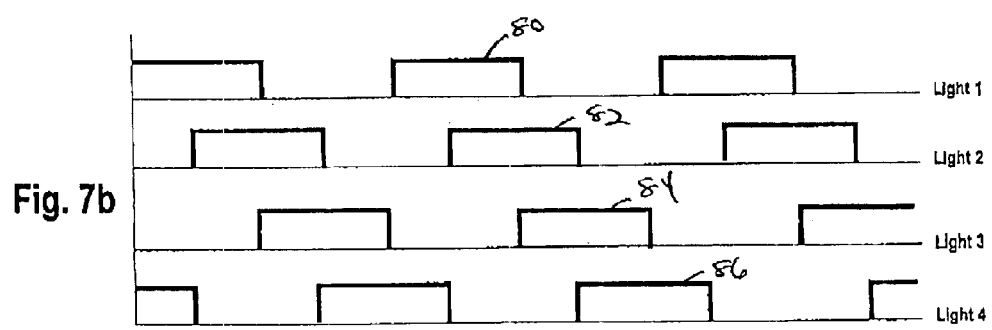
Figure 7C:
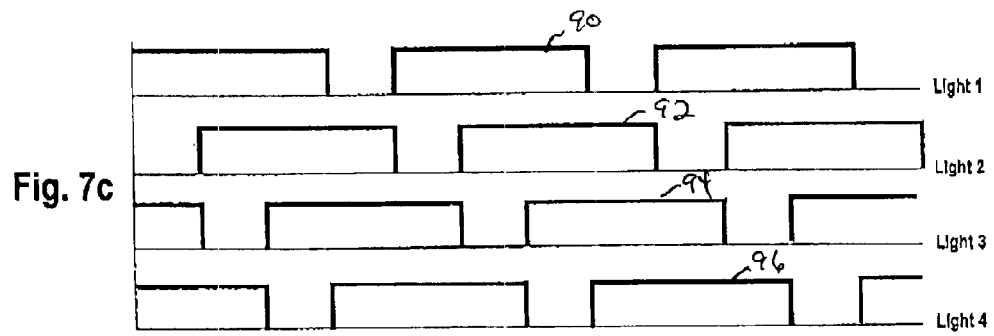

Finally, with reference to FIGS. 7a-7c, there is depicted a schematic representation of the output of pulse width modulated power supply 74 for a sample system having four light sources. As illustrated within FIG. 7a, a voltage pulse having a 25% duty cycle is output with the timing depicted in FIG. 7a so that, of four lighting sources within the illustrated lighting pod 46 only one-fourth of the maximum light intensity is available. Thus, voltage pulses 70, 72, 74 and 76 will thus, in turn, illuminate one of four lighting sources within lighting pod 46.

Similarly, with respect to FIG. 7b, voltage pulses 80, 82, 84 and 86 are generated, each having a 50% duty cycle. Thus, at any given time 50% of the lighting intensity from lighting pod 46 will be available.

Finally, with respect to FIG. 7c, voltage pulses having a duty cycle of 75% are illustrated at reference numerals 90, 92, 94 and 96. Thus, at any given time 75% of the light intensity of lighting pod 46 can be generated.

Those having ordinary skill in the art will appreciate that there remain two simple cases of the output of pulse width modulated power supply 74 which are not illustrated herein. Specifically, no voltage output during which time no light intensity is generated by a lighting pod 46 and a 100% duty cycle voltage pulse wherein 100% of the light intensity is available.

Upon reference to the foregoing, those skilled in the art will appreciate that lighting apparatus 10 of the present invention provides a technique whereby the intensity generated by a variable light intensity lighting pod 46 may be controlled by the presence or absence of an object interposed between each lighting pod 46 and work field 50. In accordance with one depicted embodiment of the present invention, the detected presence of an object interposed between a lighting pod 46 and work field 50 will cause the output of that particular lighting pod 46 to be set to zero, or decreased substantially, eliminating the possibility of shadows within work field 50 generated by that lighting pod. Substantially simultaneously, the lighting intensity of selected ones of the remaining light pods 46 will be increased from a nominal setting of 50% so that additional light is focused into work field 50 from the remaining lighting pods 46. In this manner, not only is the light directly behind an interposed object between a lighting pod 46 and work field 50 decreased, minimizing the possibility of shadows, but the lighting intensity of the remaining lighting pods is increased, further illuminating the work field in a manner which is most efficient and which requires no physical relocation of light head 34.

In an alternate embodiment, the present invention may also find application in a situation in which a lighting pod includes, for example, ten light sources. In order to prevent shadows such a lighting pod would typically be utilized with only five of those lighting sources illuminated. Thereafter, if the light from one of the lighting sources which is energized is blocked by an object interposed between the lighting source and the work field, power to that lighting source can be reduced or eliminated and one of the lighting sources which was not previously energized can be energized to maintain the original level of illumination and substantially eliminate any shadows which might result.

Similarly, the present invention can also be utilized in a reflective single light source surgical light in which a single linear light source is utilized in combination with a parabolic reflector or series of prismatic lenses. In this embodiment of the present invention multiple proximity sensors are placed in various locations within the light housing. These proximity sensors would then detect objects interposed between the reflected light rays from the parabolic reflector or prismatic lenses to the work field from the single light source. In this embodiment the light source would operate nominally at 50% power and thereafter, for example, if 10% of the light rays reflected from the parabolic reflector are blocked by an object interposed between the light fixture and the work surface power to the light source can be increased to 60%. Similarly, if 20% of the light rays reflected from the parabolic reflector or prismatic lenses onto the work field are blocked by an object interposed between the light and the work field, power to the single light source can be increased to 70%. In this manner, the amount of illumination within the work field can be maintained in a relatively constant fashion while minimizing shadows within the work field.

The embodiments and examples set forth herein are presented in order to best explain the present invention and its practical application and, thereby, to enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed. Many modifications and variations are possible in light of the above teaching without departing from the spirit and scope of the following claims.

What is claimed is:

1. An improved lighting apparatus comprising:
   a plurality of variable intensity lighting pods, each lighting pod focused on a work field and disposed along a radius extending from the work field;
   a proximity sensor within each lighting pod for detecting objects interposed between the light pod and the work field; and
   a power control circuit coupled to each lighting pod and each proximity sensor for varying the light intensity of particular variable intensity lighting pods in response to objects interposed between selected lighting pods and the work field by decreasing the light intensity of each lighting pod having an object interposed between that lighting pod and the work field such that shadows within the work field are minimized.

2. The improved lighting apparatus according to claim 1, wherein each of said plurality of variable intensity lighting pods comprises a plurality of light emitting diodes.

3. The improved lighting apparatus according to claim 2, wherein each of said plurality of light emitting diodes is a white light emitting diode.

4. The improved lighting apparatus according to claim 1, wherein each of said plurality of variable intensity lighting pods comprises a plurality of halogen light sources.

5. The improved lighting apparatus according to claim 1, wherein each proximity sensor comprises an infrared proximity sensor.

6. The improved lighting apparatus according to claim 1, wherein each proximity sensor comprises an ultrasonic sensor.

7. The improved lighting apparatus according to claim 1, wherein each of said plurality of variable intensity lighting pods is powered by an output of a pulse width modulated power supply.

8. The improved lighting apparatus according to claim 7, wherein said power control circuit comprises means for varying the output of said pulse width modulated power supply.

9. The improved lighting apparatus according to claim 8, wherein said power control circuit decreases power to any variable intensity lighting pod having an object interposed between the lighting pod and the work field.

10. The improved lighting apparatus according to claim 9, wherein said power control circuit decreases power to any variable intensity lighting pod having an object interposed between the lighting pod and the work field while increasing power to selected unlocked lighting pods.

11. The improved lighting apparatus according to claim 1, wherein said improved lighting apparatus comprises a plurality of parabolic light heads, each of said plurality of parabolic light heads including a plurality of variable intensity lighting pods mounted therein.

12. The improved lighting apparatus according to claim 11, wherein each of said plurality of parabolic light heads is mounted at one end of a variable positionable support arm.

13. An improved lighting apparatus comprising:
    variable intensity lighting pod focused on a work field and disposed along radius extending from the work field;
    a proximity sensor within the lighting pod for detecting objects interposed between the light pod and the work field; and
    a power control circuit coupled to the lighting pod and the proximity sensor for varying the light intensity of the variable intensity lighting pod in response to objects interposed between the lighting pod and the work field increasing power to the variable intensity lighting pod in response to detection of an object interposed between the lighting pod and the work field such that shadows within the work field are minimized.

14. The improved lighting apparatus according to claim 13, wherein the variable intensity lighting pod comprises a halogen light source.

15. The improved lighting apparatus according to claim 13, wherein the proximity sensor comprises an infrared proximity sensor.

16. The improved lighting apparatus according to claim 13, wherein the proximity sensor comprises an ultrasonic sensor.

* * * * *

UNITED STATES PATENT AND TRADEMARK OFFICE
CERTIFICATE OF CORRECTION

PATENT NO. : 6,880,957 B2
DATED : April 19, 2005
INVENTOR(S) : Mark Wayne Walters It is certified that error appears in the above-identified patent and that said Letters Patent is hereby corrected as shown below:

Column 6,
Line 40, after "along" and before "radius" insert -- a --.

Signed and Sealed this

Twenty-third Day of May, 2006

JON W. DUDAS
*Director of the United States Patent and Trademark Office*